US00PP29315P3

(12) United States Plant Patent
Nakashima

(10) Patent No.: US PP29,315 P3
(45) Date of Patent: May 29, 2018

(54) ROSE PLANT NAMED 'RNF YELLOW 01'

(50) Latin Name: ***Rosa* L.**
Varietal Denomination: RNF Yellow 01

(71) Applicant: Kaneya Co., Ltd., Chita, Aichi (JP)

(72) Inventor: Hitoshi Nakashima, Gifu (JP)

(73) Assignee: Kaneya Co., Ltd., Aichi (JP)

( * ) Notice: Subject to any disclaimer, the term of this patent is extended or adjusted under 35 U.S.C. 154(b) by 61 days.

(21) Appl. No.: 14/999,309

(22) Filed: Apr. 22, 2016

(65) Prior Publication Data

US 2017/0311496 P1 Oct. 26, 2017

(51) Int. Cl.
*A01H 5/02* (2018.01)

(52) U.S. Cl.
USPC ..... Plt./104
CPC ..... *A01H 5/0222* (2013.01)

(58) Field of Classification Search
USPC ..... Plt./104
See application file for complete search history.

(56) References Cited

PUBLICATIONS

UPOV hit on rose plant named 'RNF Yellow 01', JP PBR 23565, Jun. 4, 2012.*

* cited by examiner

*Primary Examiner* — Anne Marie Grunberg
(74) *Attorney, Agent, or Firm* — The Webb Law Firm

(57) ABSTRACT

A new and distinct rose plant having a strong fragrance and creamy yellow to lemon yellow-colored flowers.

4 Drawing Sheets

Botanical classification: *Rosa* L.
Varietal denomination: 'RNF Yellow 01'.

BACKGROUND OF THE INVENTION

The present invention comprises a new and distinct cultivar of rose plant known by the varietal name 'RNF Yellow 01'. The new variety was discovered in April of 2010 in Gifu, Japan. The new variety is the result of a planned breeding program between *Rosa* L. variety 'Gold Bunny' (female parent, U.S. Plant Pat. No. 4,625) and an unnamed and unpatented *Rosa rugosa* variety (male parent) from the breeder's own collection. 'RNF Yellow 01' has a different flower color than its female parent in that the flowers of 'Gold Bunny' generally have an overall bright, lemon yellow color, while the flowers of the present variety generally have a creamy yellow color on the upper surface of the petals and a lemon yellow color on the lower surface of the petals. Additionally, 'RNF Yellow 01' exhibits a fragrance like its male parent, but differs from its male parent in its actual fragrance. When 'RNF Yellow 01' is compared to *Rosa* L. 'JAChal' (U.S. Plant Pat. No. 11,883, Japanese Patent No. 13281), the varieties are similar in flower color, not having eyes on their flowers, and in that they exhibit double flowers. However, when compared to 'JAChal', 'RNF Yellow 01' has a larger flower size, different number of petals, and exhibits a fragrance. When generally compared to other rose varieties known to the breeder, the new variety differs in its strong fragrance, its type of fragrance, and in flower color. 'RNF Yellow 01' has been trial and field tested and has been found to retain its distinctive characteristics and remain true to type through successive propagations.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
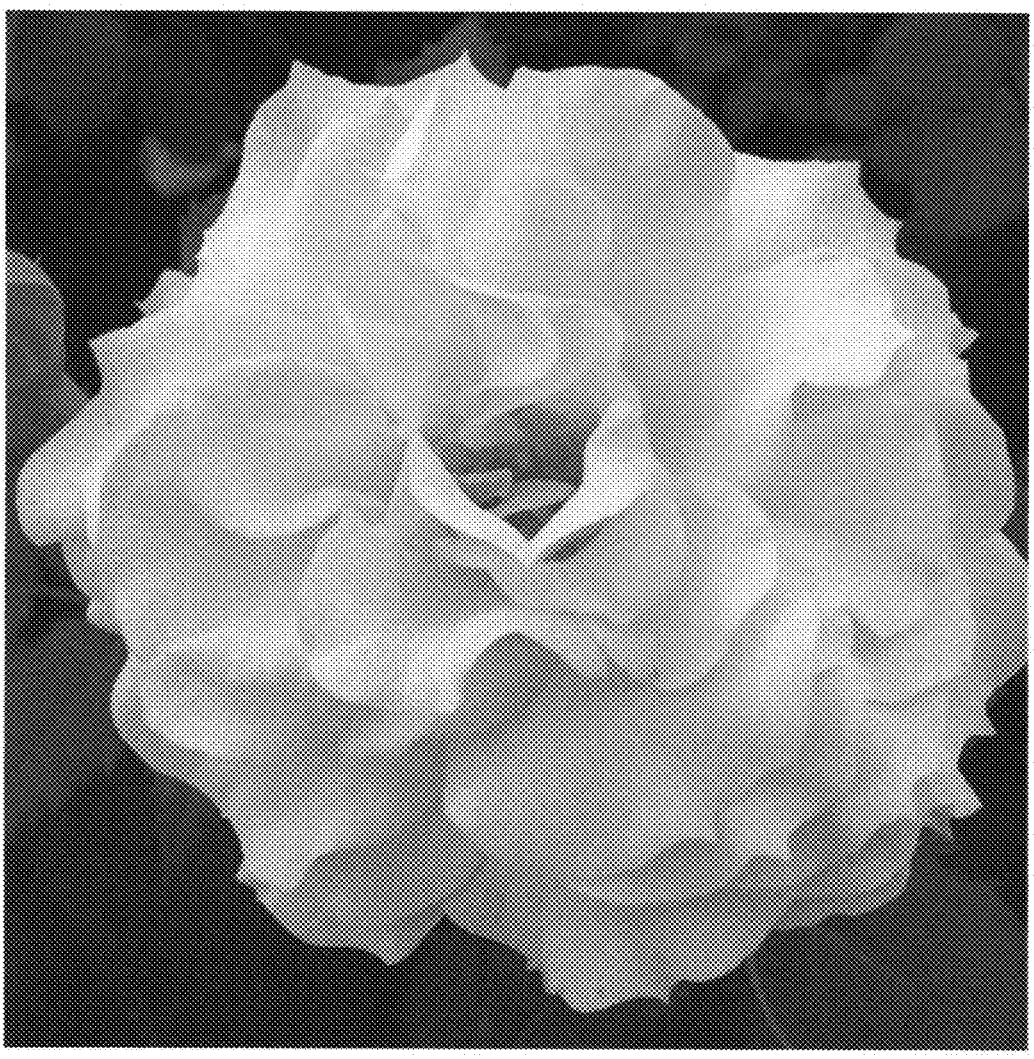
FIG. 1 shows a close-up view of a flower of the new variety.
Figure 2:
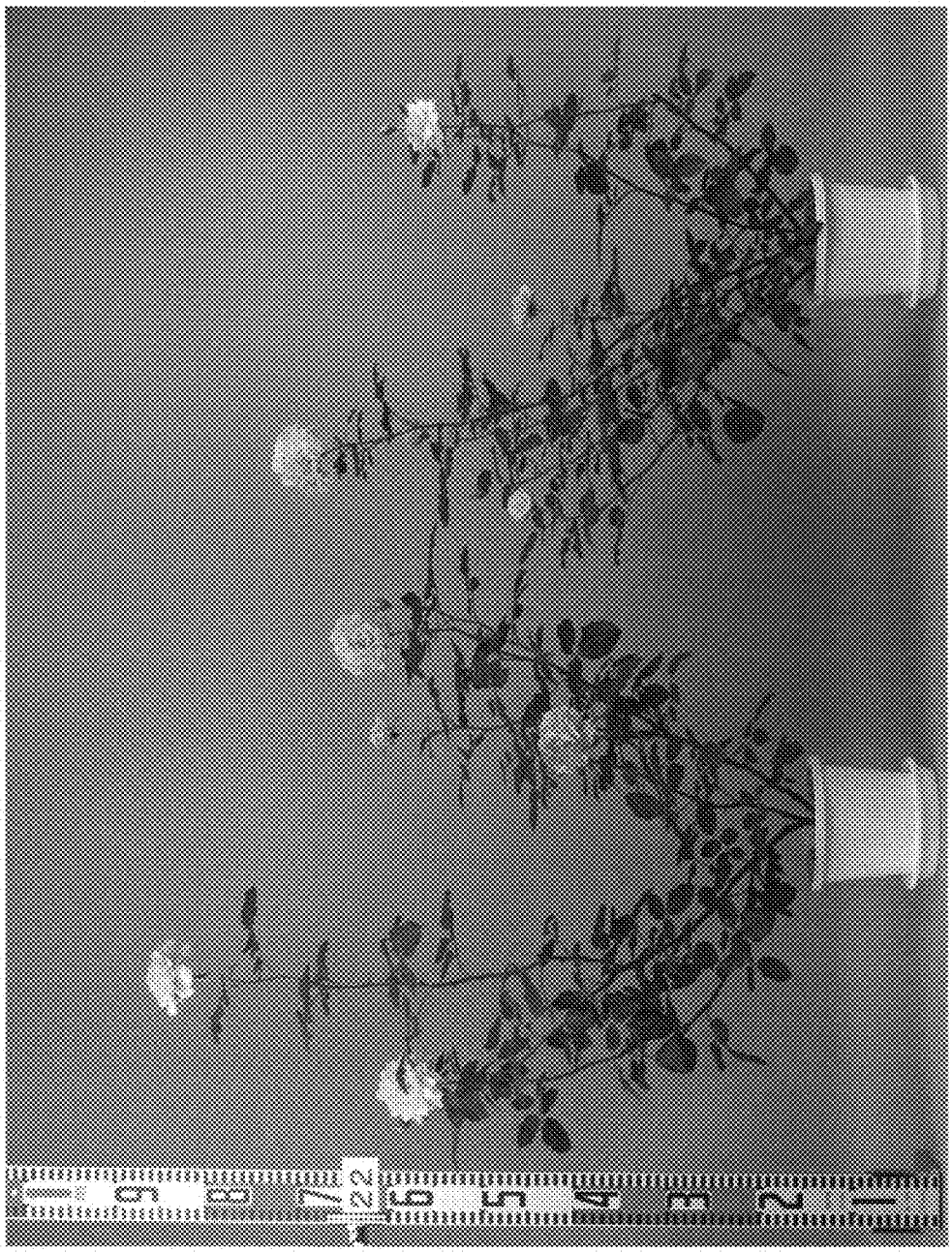
FIG. 2 shows a view of multiple plants of the new variety.
Figure 3:
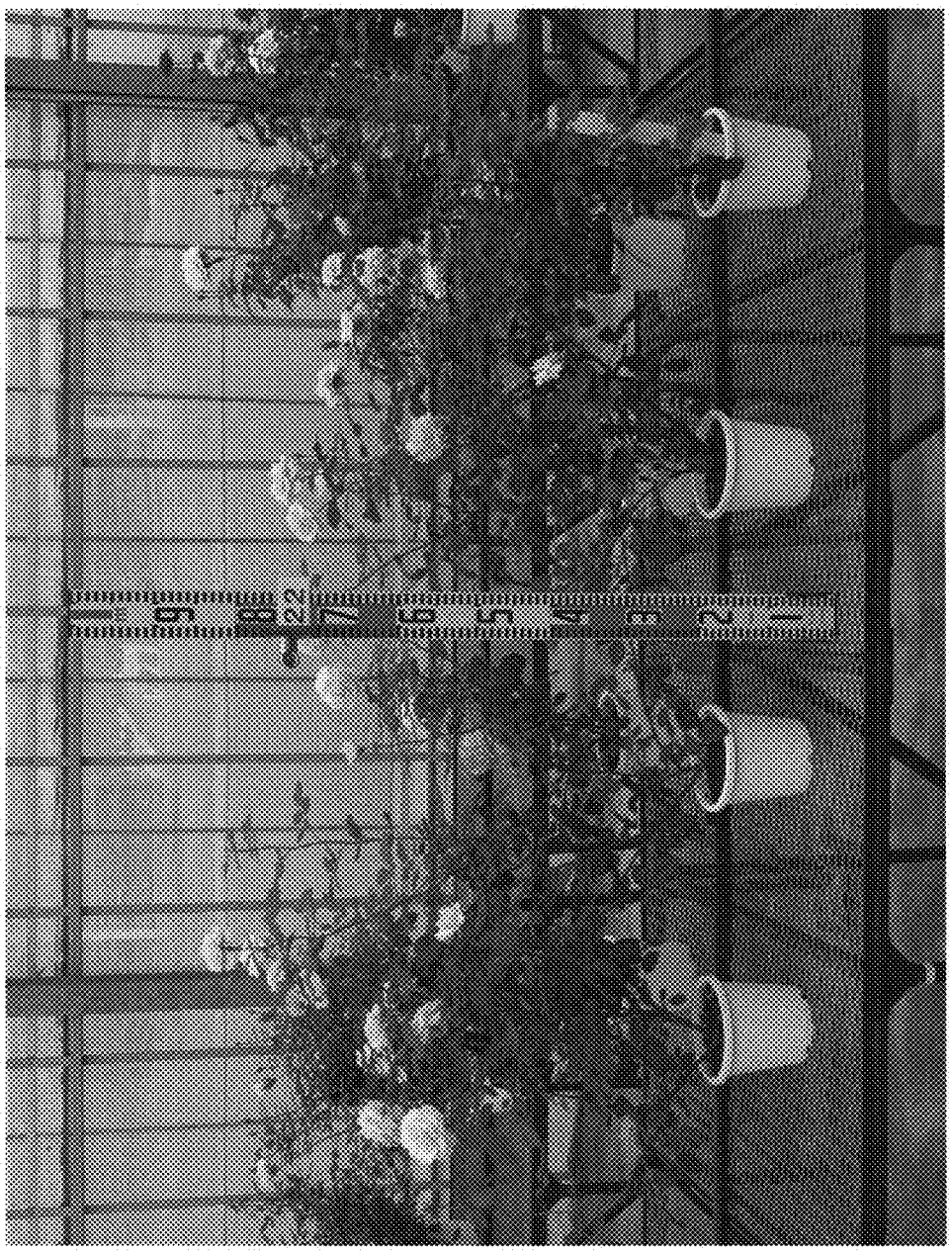
FIG. 3 shows a view of multiple plants of the new variety.
Figure 4:
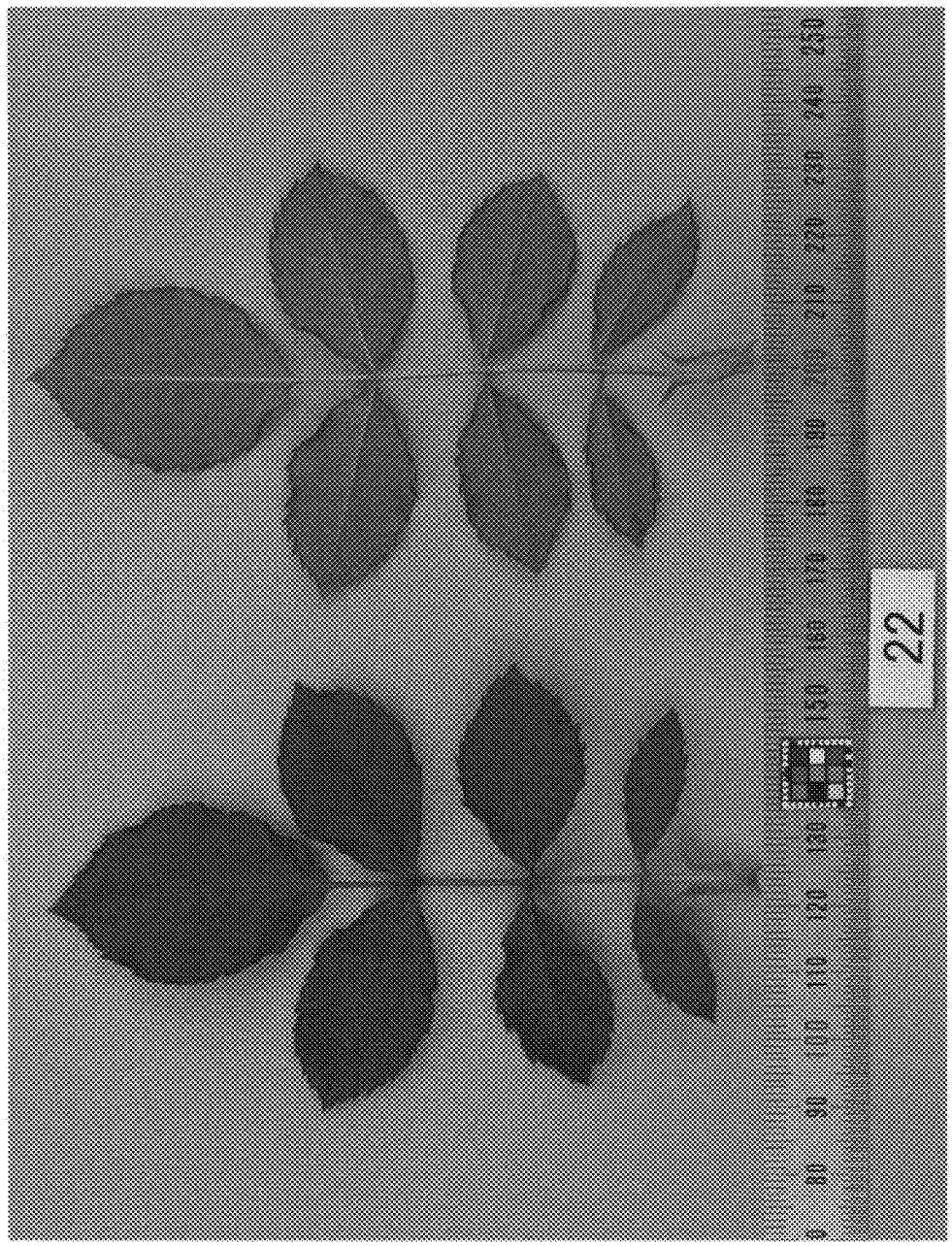
FIG. 4 shows the leaves of the new variety.

The following detailed description sets forth the characteristics of the new cultivar. The data which defines these characteristics were collected by asexual reproductions first performed via cuttings in May of 2011 carried out in Gifu, Japan. Plants of the new variety were grown in a greenhouse under natural light in 15 cm pots with peat moss substrate and with the assistance of heaters in the winter. The color readings and measurements were taken indoors in a greenhouse under natural light on one year old plants grown in containers. Color references are primarily to The R.H.S. Colour Chart of The Royal Horticultural Society of London.

Plant:

*Time to initiate roots.*—About 21-28 days at approximately 25° C.

*Time to develop roots.*—About 30-45 days at approximately 25° C.

*Time to produce a finished flowering plant from a rooted cutting.*—About 5 months/20-22 weeks in a 15 cm container.

*Rooting habit.*—Similar to standard roses.

*Form.*—Upright.

*Distance from media surface to top of foliage.*—30-35 cm at the end of production.

*Distance from media surface to top of flowers.*—35-40 cm.

*Plant diameter.*—Around 25 cm.

*Vigor*.—Average.

*Strength* (*need for artificial support*).—No artificial support needed.

*Branching characteristics*.—Branching from bottom or lower level.

*Stem color*.—Immature: 134C. Mature: 134C.

*Surface texture*.—Young wood: Similar to standard roses. Older wood: Similar to standard roses.

*Average stem diameter*.—From 7 mm to 1 cm.

*Internode length*.—Approximately 4 to 5 cm.

*Number of internodes*.—6 to 7.

*Thorns*.—Average number: Main branches: 130 per plant. Stems: 20 per stem. Length: 7 mm to 1 cm. Width: Around 5 mm. Color: 65B. Shape: Similar to standard roses.

*Foliage*.—Arrangement: Alternate. Average number of leaves per lateral branch: 7. Average number of leaflets per leaf: 7. Overall size of leaf: Length: 10 cm. Width: 5 cm. Leaflet: Shape of leaf (generally): Ovate and similar to standard roses. Shape of apex: Acute and similar to standard roses. Shape of base: Slightly obtuse to acute and similar to standard roses. Length range: 5-7 cm. Width range: 3-5 cm. Texture: Similar to standard roses. Margin type: Serrate and similar to standard roses. Color: Young leaves: Upper surface: 142A with a red edge. Lower surface: 141D with a red edge. Mature leaves: Upper surface: NN137A. Lower surface: 134C. Veins: Venation type: Pinnate and similar to standard roses. Color: Upper Surface: 137C. Lower Surface: 138B. Petiole: Length: 2-3 mm. Diameter: 1-2 mm. Color: 141D with a hint of red. Texture: Similar to standard roses. Stipule: Length: 13 mm. Width: 11.9 mm. Color: 143A. Texture: Smooth. Margin: Tiny prickles present. Apex: Symmetrical and large spear shape with small thorns present.

Inflorescence:

*Buds*.—Number of buds per plant: Average of 10 to 15 when blooming, which occurs three times per year. Number of buds per flowering stem: Generally, 2 to 4. Shape of individual bud: Napiform and similar to standard roses. Length of individual bud: 1.5-2 cm. Width of individual bud: 8 mm to 1 cm. Bud color: Green with yellow lime (2A).

*Natural flowering season at specified location*.—End of April to May in Gifu, Japan.

*Average number of flowers per year at specified location*.—Total of 30 to 45.

*Flowering habit*.—Continuous and freely flowering.

*Flower description*.—Generally, 2 to 4 flowers per flowering stem that bloom at approximately the same time.

*Lastingness of an individual flower on the plant*.—10 days to 2 weeks.

*Lastingness of a cut flower*.—1 week.

*Flower*.—General appearance: Double flowering rose. Shape: Round and mounded. Diameter: 8-10 cm. Height: 3-4 cm.

*Petals*.—Color: Upper surface (when opening): Creamy yellow (3B to 6D with 3A present). Lower surface (when opening): Lemon yellow (2A). Upper surface (fully opened): Creamy yellow (6D). Lower surface (fully opened): Lemon yellow (2A). Shape: Rounded with fringed edges. Length: 4-5 cm. Width: 5-6 cm. Apex shape: Round with a wide lip. Base shape: Round and narrow. Margin: Entire. Number per flower: 40-45. Texture: Soft and similar to standard rose petals. Reflex characteristics: None. Presence of basal petal spots: None. Petaloid description: Lightly fringed with semi-double flowering.

*Sepals*.—Color: Upper surface (when opening): N138B. Lower surface (when opening): N138B. Upper surface (fully opened): 139C. Lower surface (fully opened): 144A. Shape: Sharp. Length: 2-3 cm. Width: 8 mm to 1 cm. Apex shape: Pointed. Base shape: Wide. Margin: Entire and tight, when closed. Number per flower: 4-5. Texture: Similar to standard roses.

*Pedicel*.—Length: 3-5 cm. Diameter: 3 mm. Texture: Similar to standard roses. Strength: Strong. Color: 142A.

*Peduncle color*.—141C.

*Receptacle*.—Texture: Same as a standard Floribunda-type rose. Shape: Same as a standard Floribunda-type rose. Height: 5-7 mm. Width: 5-7 mm. Color: 141C.

*Fragrance*.—Strong.

*Disease/pest resistance*.—Average, nothing unusual noted to date.

*Cold temperature tolerance*.—During the natural blooming season the variety exhibits a cold temperature tolerance to 7° C.

*Hot temperature tolerance*.—40° C.

*Drought tolerance*.—Average.

*Reproductive organs*.—

*Stamens*.—Number (per flower): 50. Filament: Length: 7-10 mm. Color: Orange. Anthers: Shape: Like a match stick. Length: 2-3 mm. Color: Orange. Pollen: Color: 17A. Amount (generally): Less than average.

*Pistils*.—Number: 50. Length: 1-2 mm. Style: Length: Average. Color: Orange. Stigma: Shape: Similar to standard roses. Color: Orange. Size: 1 mm. Ovaries: Length: 3 mm. Width: 0.5 mm. Color: White.

I claim:

1. A new and distinct variety of rose plant, as is herein illustrated and described.

* * * * *